United States Patent [19]

Kwon et al.

[11] Patent Number: 5,801,254
[45] Date of Patent: Sep. 1, 1998

[54] ARTEMINOLIDE DERIVATIVES AND PROCESS FOR THE MANUFACTURE THEREOF

[75] Inventors: Byoung-Mog Kwon; Song-Hae Bok, both of Daejeon; Seung-Ho Lee, Cheongju-shi; Young-Kook Kim, Daejeon; Mi-Jeong Kim, Daegu; Jongheon Shin; Youngwan Seo, both of Ansan-shi; Soo-Ik Chang, Cheongju-shi, all of Rep. of Korea

[73] Assignee: Korea Institute of Science and Technology, Seoul, Rep. of Korea

[21] Appl. No.: 906,612

[22] Filed: Aug. 5, 1997

[30] Foreign Application Priority Data

Aug. 6, 1996 [KR] Rep. of Korea .................. 96-32714
Mar. 13, 1997 [KR] Rep. of Korea .................. 97-8517

[51] Int. Cl.$^6$ ............................................... C07D 307/94
[52] U.S. Cl. ............................................... 549/265
[58] Field of Search ................................... 549/265

[56] References Cited

PUBLICATIONS

Jakupovic et. al., Phytochemistry, vol. 26 (10), pp. 2777–2779, 1987.

*Primary Examiner*—Bernard Dentz
*Attorney, Agent, or Firm*—Anderson Kill & Olick, P.C.

[57] ABSTRACT

Arteminolides obtained from *Artemisia sylvatica* MAXIMOWICZ and having a core structure of formula (I) or an isomeric structure thereof are effective farnesyl-protein transferase inhibitors as well as angiogenesis suppressors, and, accordingly, they are useful for the treatment of various cancers and angiogenesis-related diseases.

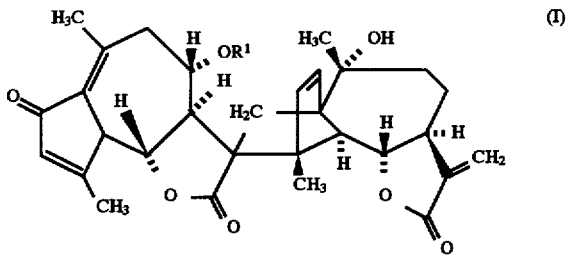

3 Claims, 6 Drawing Sheets

ARTEMINOLIDE DERIVATIVES AND PROCESS FOR THE MANUFACTURE THEREOF

FIELD OF THE INVENTION

The present invention relates to arteminolide compounds obtained from an Artemisia plant; and, more particularly, to novel arteminolide derivatives extracted from *Artemisia sylvatica* MAXIMOWICZ which are effective in inhibiting farnesyl-protein transferase("FPTase") as well as in suppressing angiogenesis; to a process for the preparation thereof; and to a pharmaceutical composition containing same.

BACKGROUND OF THE INVENTION

Hitherto, there have been made extensive efforts to develop effective anticancer agents capable of repressing the expression of oncogenic genes.

Certain of such efforts has resulted in the discovery that a well-known oncogenic gene, ras oncogene, is activated in about 30% of human cancer cells. In order to transform cells, the Ras protein must bind to the plasma membrane; and, for this binding to occur, a farnesyl group must be attached to the C-terminus thereof. Thus, it has been expected that inhibition of the FPTase involved in such farnesylation step could repress the expression of ras oncogene.

The Ras protein produced by the expression of ras proto-oncogene has a molecular weight of 21 kDa and consists of 188–189 amino acid residues. It is capable of binding with guanine nucleotides (GDP and GTP) to act as a signal transmitting agent to growth factors. The ras oncogene, which is the first oncogenic gene found in human carcinomas, is classified into harvey-ras (H-ras), kirsten-ras (K-ras) and N-ras. More than 30% of the human cancer cells examined were found to contain mutated ras genes which produce Ras proteins (H-Ras, K-Ras and N-Ras) of abnormal biological activities. In particular, mutated ras genes have been found in 90% of exocrine pancreatic carcinoma, 50% of colon carcinoma and 50% of lung cancer cases (M. Barbacid, *Ann. Rev. Biochem.*, 56, 779(1987)).

Normal Ras proteins are involved in the regulation of growth and division in animal cells; and, like other G-proteins, must bind with GTP to become activated or "switched on" as a signal transmitting agent, while it becomes deactivated or "switched off" when the GTP bound thereto gets hydrolyzed to GDP (G. Bollag, *Ann. Rev. Cell Biol.*, 7, 601(1991)).

Biochemical and structural studies have suggested that after binding with GTP, the Ras protein must be localized in the plasma membrane in order to perform its intended biological function. For the Ras protein to become functional by attaching itself to the plasma membrane, the precursor protein must bind with lipids, more specifically, with isoprenoid derivatives generated in the steroid biosynthesis, through a series of reactions called post-translational modifications. Such lipid binding reaction, i.e., farnesylation, occurs at the cysteine residue site of the C-terminus of Ras protein containing a sequence motif expressed by CAAX, wherein C is cysteine, A is an aliphatic amino acid and X is Ser, Ala, Met or Glu which serves as the recognition site for the FPTase.

The above mentioned binding of a farnesyl group to the cysteine residue of the Ras C-terminus represents the first step of the post-translational modifications, which is followed by proteolytic cleavage of the three amino acid residues, AAX; and, finally, the cysteine residue exposed at the C-terminus is methylated. The Ras protein thus modified has a lipophilic C-terminus which interacts strongly with the plasma membrane.

The post-translational modifications described above involve three enzymes which control the farnesyl group transfer, the peptide hydrolysis and the methylation steps, respectively. An agent which suppresses the post-translational modifications by inhibiting one of the three enzymes is expected to be an effective anticancer drug. Along this line, therefore, there have been extensive studies to develop inhibitors of the enzymes for the post-translational modifications, particularly those of FPTase.

It has been observed that the FPTase isolated from mice is inhibited by compounds having the structural feature of the C-terminus of a Ras protein. Based on this observation, a number of peptide derivatives having a terminus sequence of CAAX have been synthesized and screened for their inhibitory activities (Y. Reiss, *Cell*, 62, 81(1990)). As a result, effective farnesyl-protein inhibitors designated as L-731,734 and L-731,735 have been developed by Merck (N. E. Kohl et al., *Science*, 260, 1937(1993)). Meanwhile, a benzodiazepin derivative having a good inhibitory activity has been discovered by Genentech (G. L. James et al., *Science*, 260, 1937(1993)). Also, Merck has announced a developmental inhibitor designated L-744,822 which exhibits a strong anti-tumor activity against carcinoma induced by transplanting ras oncogenes into nude mice (N. E. Kohl et al., *Nature Med.*, 1, 792(1995)).

There have also been many screening studies to identify natural products which may exhibit an inhibitory activity against farnesyl-protein transferase. Among those reported to have such activity are: limonene, perillic acid and dihydroperillic acid of plant-origin; 10'-desmethoxystretonigrin isolated from actinomyces; chaetomellic acid A and B isolated from the culture of *Chaetomella acutiseta;* and zaragozic acid A and B which were earlier recognized to be squalene synthase inhibitors. Other compounds reported to be FPTase inhibitors are pepticinnamins and diepoxybenz[a]anthracene (V. Manne et al., *Drug Devel. Res.*, 34, 121(1995); S. Omura et al., *Drug Future*, 19, 751(1994)).

On the other hand, angiogenesis, a process of forming new blood vessels extending from existing veins, occurs during the development and metastasis of cancer cells. As reported, this process may be facilitated by a factor called angiogenin isolated from the secretion of HT-29 human colon carcinoma cells (Vallee et al., *Biochemistry*, 24, 5480 (1985)), while angiostatin, one of anti-angiogenic factors which suppress angiogenesis, may inhibit the growth and metastasis of lung cancer cells (M. S. O'Relly et al., *Cell*, 79, 715(1994)). Examples of other anti-angiogenic factors are: alpha interferon which protects new born babies from lung angioma; antibodies of vascular enthothelial growth factor; an anti-prostate cancer agent named genistein which is a natural product isolated from soy beans; platelet factor-4 and its peptide derivative; fumagillin and its derivative; ursolic acid; Herbimycin A; cartilage-derived inhibitor; and a synthetic compound named ovalicine.

As described above, there have been reported various FPTase inhibitors as well as angiogenesis inhibitors, however there has continued to exist a need for an improved new FPTase inhibitor and for a new improved angiogenesis inhibitor. It is particularly desirable to develop an agent which is effective in inhibiting both farnesyl-protein transferase and angiogenesis: such agent would be especially useful for the prevention and treatment of various cancers and also for the treatment of angiogenesis-related diseases, e.g., rheumatism, diabetic retinopathy, chronic inflammation, retinitis and angioma.

SUMMARY OF THE INVENTION

Accordingly, it is an object of the present invention to provide novel arteminolide derivatives which inhibit farnesyl-protein transferase(FPTase) and suppress angiogenesis.

It is another object of the present invention to provide a process for the preparation of said arteminolide derivatives.

It is a further object of the present invention to provide a pharmaceutical composition containing said arteminolide derivatives in an effective amount for the treatment of various cancers and angiogenesis-related diseases.

In accordance with one aspect of the present invention, there is provided an arteminolide compound of formula (I) or (II):

wherein $R^1$ is and $R^2$ is

BRIEF DESCRIPTION OF THE DRAWINGS

The above and other objects and features of the present invention will become apparent from the following description of the invention taken in conjunction with the following accompanying drawings; wherein.

DETAILED DESCRIPTION OF THE INVENTION

Figure 1A:
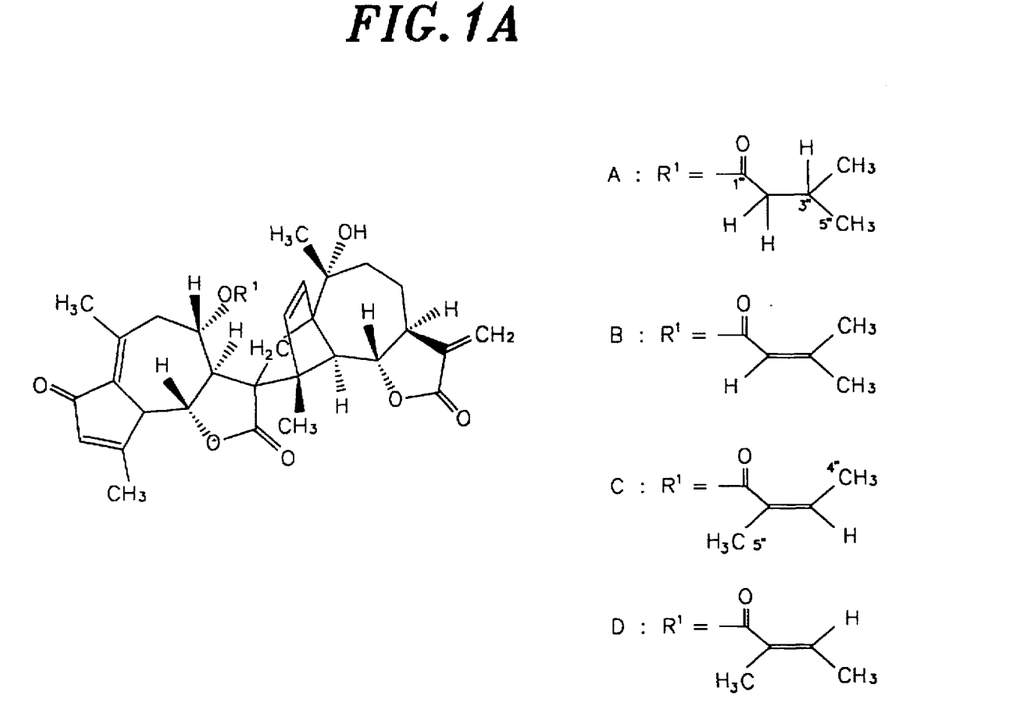
FIG. 1 shows the structure of arteminolides.
Figure 1B:
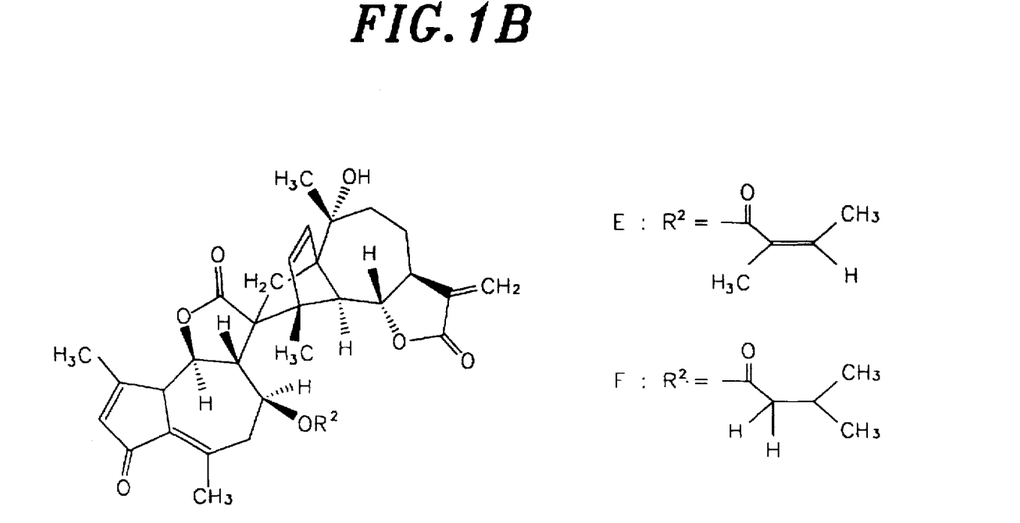

The present invention discloses six novel arteminolides which have inhibitory activities against farnesyl protein transferase and angiogenesis. The structural features of these six arteminolides are shown in FIG. 1 and they are designated as arteminolides A, B, C, D, E and F, respectively.

The physicochemical properties of arteminolides A, B, C, D, E and F are listed in Tables 1, 2, 3, 4, 5 and 6, respectively.

TABLE 1

The Physicochemical Properties of Arteminolide A

| Physicochemical Properties | Arteminolide A |
|---|---|
| Appearance | non-color solid |
| Polarizing degree ($[\alpha]_D$ in CHCl$_3$) | +15° |
| Molecular formula | $C_{35}H_{42}O_8$ |
| Molecular weight (HREI-MS (m/z)) | |
| measured: | 591.2924 |
| calculated: | 591.2957 |
| UV absorption (UV $\lambda_{max}$ (nm)) | 212, 254 |
| IR absorption (IR $v_{max}$ (cm$^{-1}$)) | 3600, 1758.40, 1697.50, 2927, 1263 |
| Solubility | |
| soluble: | MeOH, acetone, chloroform, DMSO |
| insoluble: | hexane, H$_2$O |
| Melting Point | 195° C. |

TABLE 2

The Physicochemical Properties of Arteminolide B

| Physicochemical Properties | Arteminolide B |
|---|---|
| Appearance | non-color solid |
| Polarizing degree ($[\alpha]_D$ in CHCl$_3$) | +10° |
| Molecular formula | $C_{35}H_{40}O_8$ |
| Molecular weight (HREI-MS (m/z)) | |
| measured: | 589.2875 |
| calculated: | 589.2801 |
| UV absorption (UV $\lambda_{max}$ (nm)) | 220, 254 |
| IR absorption (IR $v_{max}$ (cm$^{-1}$)) | 3600, 1758.40, 1697.50, 2927, 1263 |
| Solubility | |
| soluble: | MeOH, acetone, chloroform, DMSO |
| insoluble: | hexane, H$_2$O |
| Melting Point | 198° C. |

TABLE 3

The Physicochemical Properties of Arteminolide C

| Physicochemical Properties | Arteminolide C |
|---|---|
| Appearance | non-color solid |
| Polarizing degree ($[\alpha]_D$ in $CHCl_3$) | +5° |
| Molecular formula | $C_{35}H_{40}O_8$ |
| Molecular weight (HREI-MS (m/z)) | |
| measured: | 589.2791 |
| calculated: | 589.2801 |
| UV absorption (UV $\lambda_{max}$ (nm)) | 215, 253 |
| IR absorption (IR $v_{max}$ ($cm^{-1}$)) | 3600, 1758.40, 1697.50, 2927, 1263 |
| Solubility | |
| soluble: | MeOH, acetone, chloroform, DMSO |
| insoluble: | hexane, $H_2O$ |
| Melting Point | 190° C. |

TABLE 4

The Physicochemical Properties of Arteminolide D

| Physicochemical Properties | Arteminolide D |
|---|---|
| Appearance | non-color solid |
| Polarizing degree ($[\alpha]_D$ in $CHCl_3$) | +25° |
| Molecular formula | $C_{35}H_{40}O_8$ |
| Molecular weight (HREI-MS (m/z)) | |
| measured: | 589.2756 |
| calculated: | 589.2801 |
| UV absorption (UV $\lambda_{max}$ (nm)) | 216, 253 |
| IR absorption (IR $v_{max}$ ($cm^{-1}$)) | 3600, 1758.40, 1697.50, 2927, 1263 |
| Solubility | |
| soluble: | MeOH, acetone, chloroform, DMSO |
| insoluble: | hexane, $H_2O$ |
| Melting Point | 195° C. |

TABLE 5

The Physicochemical Properties of Arteminolide E

| Physicochemical Properties | Arteminolide E |
|---|---|
| Appearance | non-color solid |
| Polarizing degree ($[\alpha]_D$ in $CHCl_3$) | −55° |
| Molecular formula | $C_{35}H_{40}O_8$ |
| Molecular weight (HREI-MS (m/z)) | |
| measured: | 589.2756 |
| calculated: | 589.2801 |
| UV absorption (UV $\lambda_{max}$ (nm)) | 214, 254 |
| IR absorption (IR $v_{max}$ ($cm^{-1}$)) | 3600, 1758.40, 1697.50, 2927, 1263 |
| Solubility | |
| soluble: | MeOH, acetone, chloroform, DMSO |
| insoluble: | hexane, $H_2O$ |
| Melting Point | 195° C. |

TABLE 6

The Physicochemical Properties of Arteminolide F

| Physicochemical Properties | Arteminolide F |
|---|---|
| Appearance | non-color solid |
| Polarizing degree ($[\alpha]_D$ in $CHCl_3$) | −10° |
| Molecular formula | $C_{35}H_{42}O_8$ |
| Molecular weight (HREI-MS (m/z)) | |
| measured: | 591.2915 |
| calculated: | 591.2957 |
| UV absorption (UV $\lambda_{max}$ (nm)) | 210, 254 |
| IR absorption (IR $v_{max}$ ($cm^{-1}$)) | 3600, 1758.40, 1697.50, 2927, 1263 |
| Solubility | |
| soluble: | MeOH, acetone, chloroform, DMSO |
| insoluble: | hexane, $H_2O$ |
| Melting Point | 185° C. |

The main frame structure of arteminolides A, B, C and D differs from that of arteminolides E and F only in the steric arrangement at the 1' and 4' carbons.

The arteminolide compounds of the prevent invention are extracted from *Artemisia sylvatica* MAXIMOWICZ by employing a suitable organic solvent and purified according to a general procedure described below.

Dried *Artemisia sylvatica* MAXIMOWICZ is pulverized and an organic solvent, e.g., a chloroform-acetone(1:1) mixture, is added thereto. The resulting mixture is left standing at room temperature for 2 days, stirred, and the stirred mixture is filtered to obtain an extract and a solid residue. The solid residue is extracted two more times by the same procedure. The extracts thus obtained are combined, concentrated under a reduced pressure, and the concentrated residue is extracted with an organic solvent, e.g., a methylene chloride, to obtain a crude mixture containing arteminolides. This crude mixture is refined by conducting a series of silica gel column chromatography as well as thin layer chromatography using various combinations of solvents, e.g., hexane, ethyl acetate, chloroform, methanol and water, as eluents to obtain an arteminolide concentrate.

The arteminolide concentrate thus obtained is subjected to high performance liquid chromatography using a mixture of water and methanol at a ratio ranging from 4:6 to 8:2 as an eluent to separate the arteminolides into fractions each containing pure arteminolide A, B, C, D, E or F.

The pharmaceutical composition of the present invention, which may be useful for the treatment of various cancers and angiogenesis-related diseases, may comprise pharmaceutically acceptable excipients, carriers or diluents in combination with one or more arteminolide compounds as an active ingredient. The pharmaceutical formulations may be prepared in accordance with any one of the conventional procedures.

In preparing the inventive composition, the active ingredient is preferably admixed or diluted with a carrier, or enclosed within a carrier which may be in the form of a capsule, sachet or other container. When the carrier serves as a diluent, it may be a solid, semi-solid or liquid material acting as a vehicle, excipient or medium for the active ingredient. Thus, the compositions may be in the form of a tablet, pill, powder, sachet, elixir, suspension, emulsion, solution, syrup, aerosol, soft and hard gelatin capsule, sterile injectable solution, sterile packaged powder and the like.

Examples of suitable carriers, excipients, and diluents are lactose, dextrose, sucrose, sorbitol, mannitol, starches, gum acacia, alginates, gelatin, calcium phosphate, calcium silicate, cellulose, methyl cellulose, microcrystalline cellulose, polyvinylpyrrolidone, water, methylhydroxybenzoates, propylhydroxybenzoates, talc, magnesium stearate and mineral oil. The formulations may additionally include lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

The pharmaceutical composition of the present invention can be administered by a variety of routes including oral, transdermal, subcutaneous, intravenous and intramuscular introduction. A typical daily dose of the active ingredient may range from about 5 to 10 mg/kg body weight, preferably 5 to 7 mg/kg body weight, and can be administered in a single dose or in divided doses. However, it should be understood that the amount of the active ingredient actually administered ought to be determined in light of various relevant factors including the condition to be treated, the chosen route of administration, the age and weight of the individual patient, and the severity of the patient's symptom; and, therefore, the above dose should not be intended to limit the scope of the invention in any way.

The following Examples are intended to further illustrate the present invention without limiting its scope; and the experimental methods used in the Examples can be practiced in accordance with the Reference Examples given herein below, unless otherwise stated.

Further, percentages given below for solid in solid mixture, liquid in liquid, and solid in liquid are on a wt/wt, vol/vol and wt/vol basis, respectively, unless specifically indicated otherwise.

EXAMPLE 1

Extraction and Purification of Arteminolide Compounds from *Artemisia sylvatica* MAXIMOWICZ

*Artemisia sylvatica* MAXIMOWICZ growing in central parts of the Republic of Korea was harvested and dried. About 5.0 kg of dried *Artemisia sylvatica* MAXIMOWICZ was pulverized and 20 l of chloroform-acetone(1:1) mixture was added thereto. The resulting mixture was left standing at room temperature for 48 hours and stirred. The stirred mixture was filtered to obtain an extract and a solid residue. The solid residue was extracted two more times by the same procedure. The extracts thus obtained were combined, concentrated under a reduced pressure, and the concentrated residue was extracted with 5 l of methylene chloride, and the resulting solution was concentrated under a reduced pressure to obtain 150 g of a mixture containing active substances. The mixture was diluted with 2 l of methylene chloride and subjected t8o silica gel column chromatography(3 l of silica gel(Merck, U.S.A., Art No.9385)), wherein a mixture of hexane and ethylacetate(9:1 to 3:7) was used as an eluent to remove non-polar substances, and then, a chloroform-methanol(85:15) mixture was used as an eluent to obtain a fraction having active substances, solvent was removed therefrom to obtain an extract in an amount of 100 g.

The extract thus obtained was subjected to another silica gel chromatography(2 l of silica gel) using a mixture of hexane and ethylacetate(the ratio was varied from 8:2 to 0:10) as an eluent to obtain 50 g of a mixture.

50 g of the mixture thus obtained was allowed to adsorbed on 250 g of C18 column(Merck, U.S.A., LiChroprep RP-18) and a mixture of methanol and water was fed to the column while varying the methanol to water ratio from 5:5 to 10:0 to obtain 5.8 g of a fraction which showed FPTase inhibitory activity at a concentration of 100 µg/ml.

The resulting mixture was subjected to thin layer chromatography using a mixture of chloroform and methanol (95:5) or a mixture of hexane and ethylacetate(6:4) as an eluent to obtain a fraction having an inhibitory activity of 85% or more at a concentration of 100 µg/ml.

Finally, the resulting mixture was subjected to high performance liquid chromatography(column: Phenomenex, ultracab 10 ODS(250×21,2 mm)) wherein a mixture of water and methanol was used as an eluent while varying the water to methanol ratio from 5:5 to 7:3 to obtain 3 mg, 4 mg, 10 mg, 2 mg, 3 mg and 5 mg of pure arteminolides A, B, C, D, E and F, respectively, per 1 kg of *Artemisia sylvatica* MAXIMOWICZ.

EXAMPLE 2

Structural Analysis of Arteminolides

Figure 2:
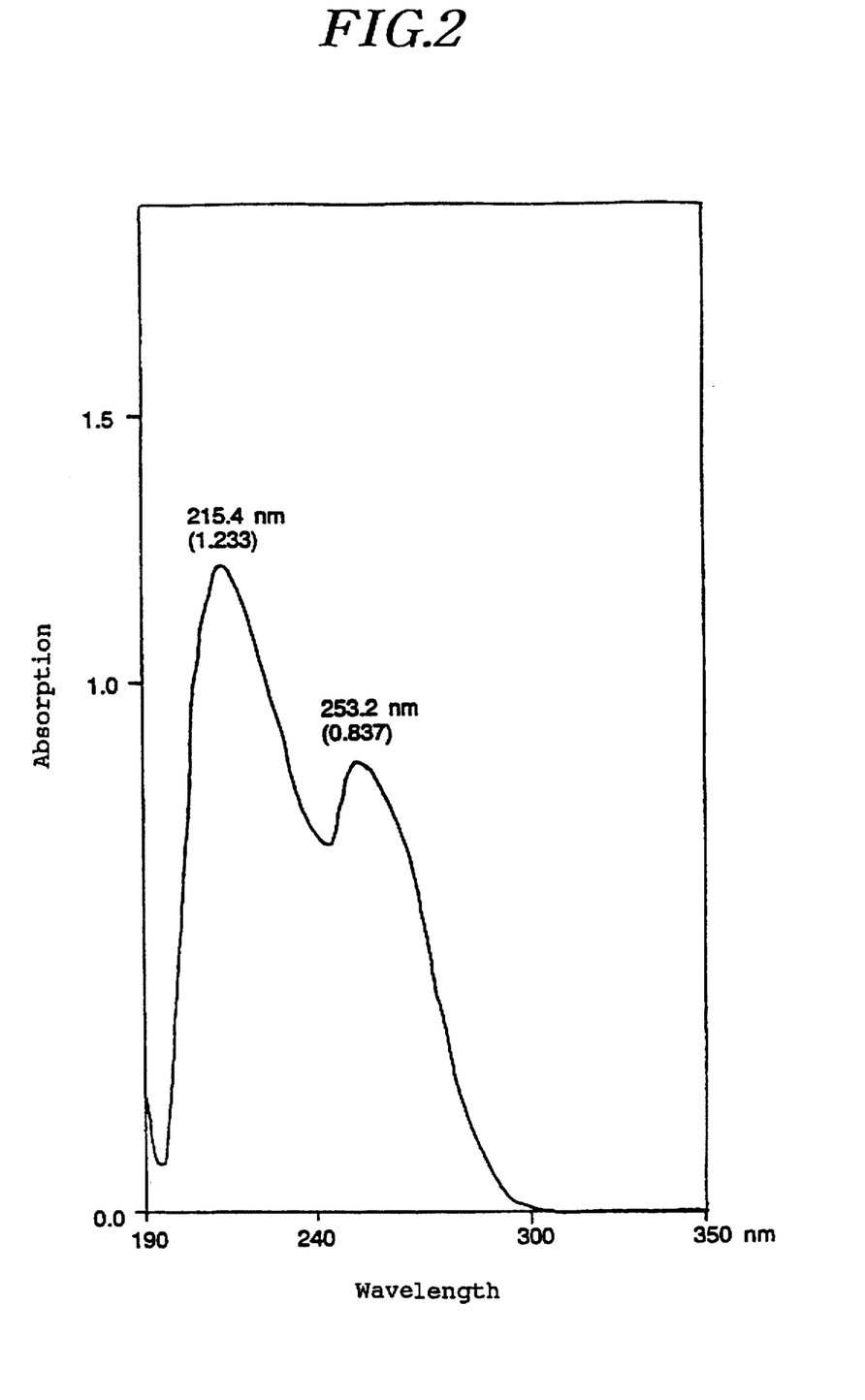
FIG. 2 provides the UV spectrum of arteminolide A.

1) UV-Visible light analysis was carried with UV-Vis spectrophotometer model UV-265(Shimadzu, Japan). The absorption maxima occurred at 215 nm and 253 nm(see FIG. 2: UV spectrum of arteminolide A).

Figure 3:
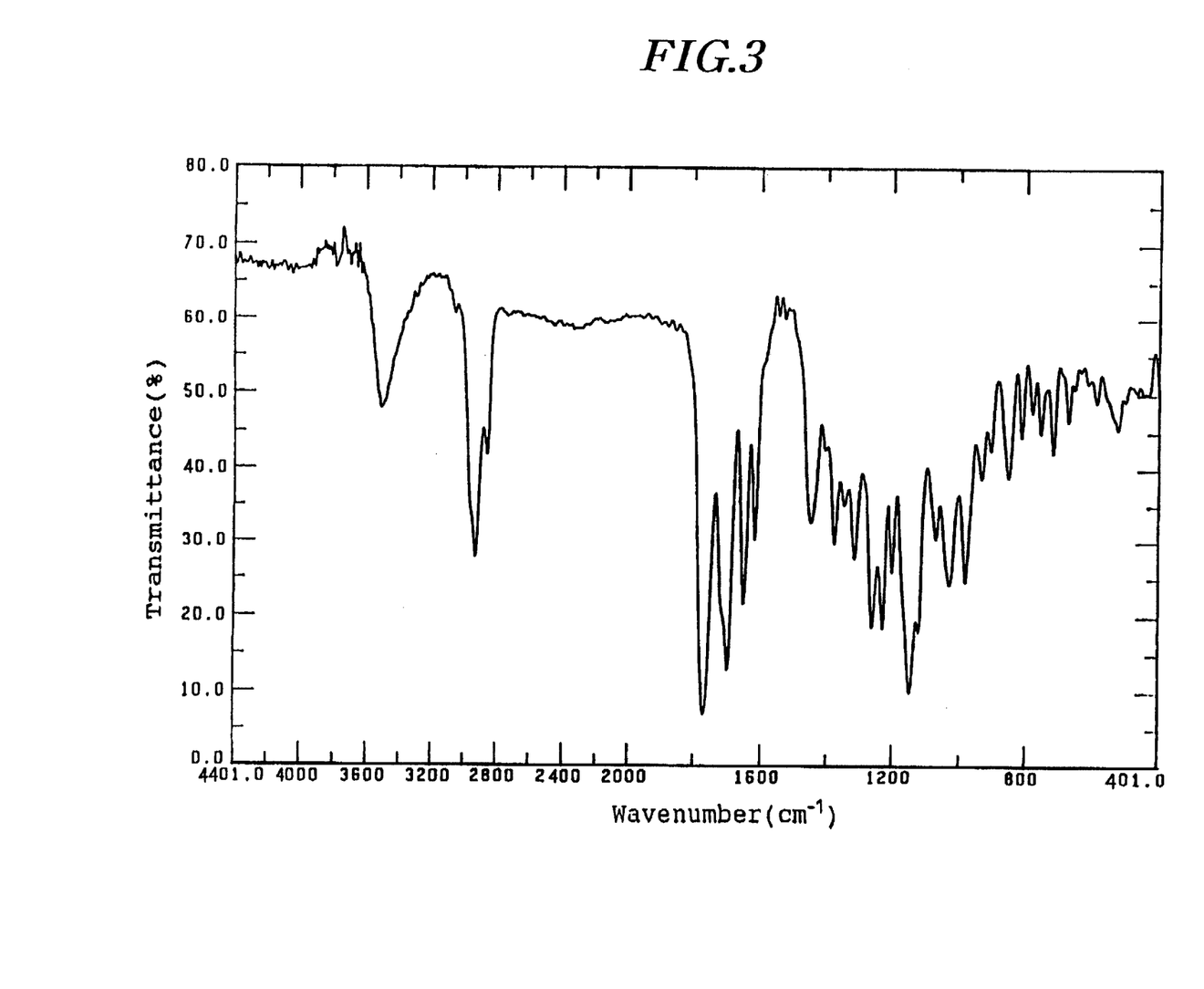
FIG. 3 displays the IR spectrum of arteminolide A.

2) IR studies conducted with an IR spectroscope(model FTS-80, Bio-Rad Digilab Division) showed the following characteristic arteminolide peaks; OH group at 3600 $cm^{-1}$, γ-lactone at 1758.40 $cm^{-1}$, C=C or C=O group at 1697.50 $cm^{-1}$, $CH_2$ group at 2927 cm–1 and C—O—C group at 1263 cm–1(see FIG. 3: IR spectrum of arteminolide A).

3) The molecular weight was determined with VG70-VSEQ mass spectrometer(Vacuum Generator, UK) by using High-Resolution Electron Impaction(HREI)-MS method. The results showed the following molecular formula; arteminolide A(molecular weight: measured 591.2924, calculated 591.2957): $C_{35}H_{42}O_8$, arteminolide B(molecular weight: measured 589.2875, calculated 589.2801): $C_{35}H_{40}O_8$, arteminolide C(molecular weight: measured 589.2791, calculated 589.2801): $C_{35}H_{40}O_8$, arteminolide D(molecular weight: measured 589.2756, calculated 589.2801): $C_{35}H_{40}O_8$, arteminolide E(molecular weight: measured 589.2756, calculated 589.2801): $C_{35}H_{40}O_8$ and arteminolide F(molecular weight: measured 591.2915, calculated 591.2957): $C_{35}H_{42}O_8$.

Figure 4:
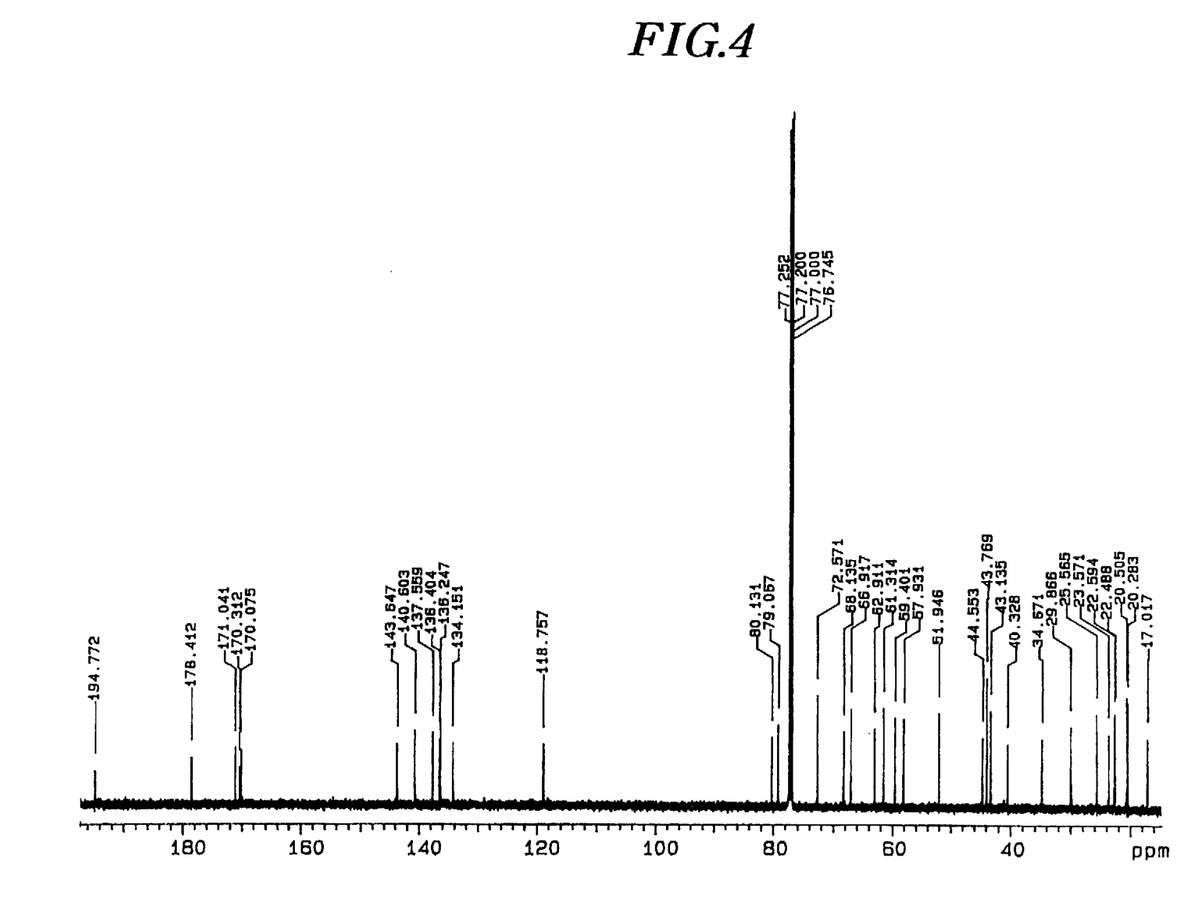
FIG. 4 depicts the $^{13}$C-NMR spectrum of arteminolide A.
Figure 5:
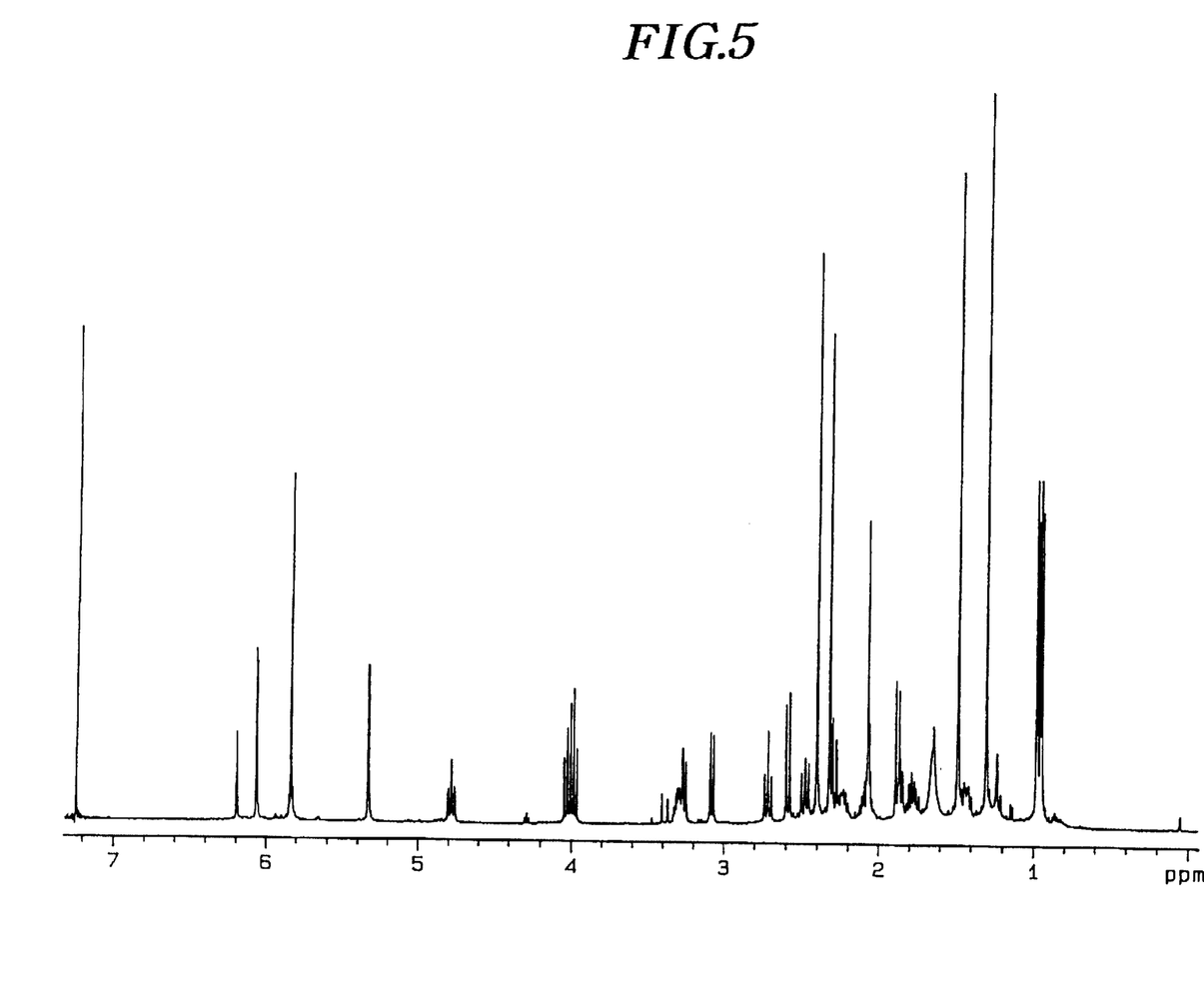
FIG. 5 illustrates the $^1$H-NMR spectrum of arteminolide A.
Figure 6:
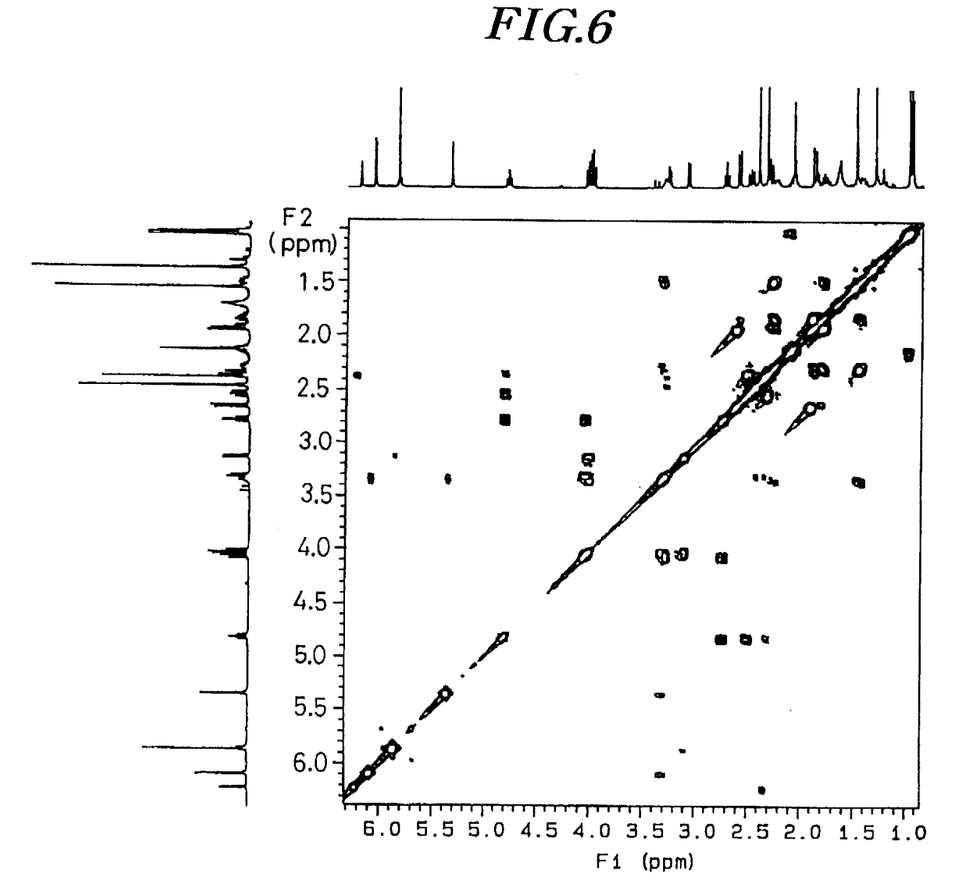
FIG. 6 represents the Cosy NMR spectrum of arteminolide A.

4) NMR analysis was carried out by using Varian 300 MHz, 500 MHz NMR. The $^1$H-NMR data, $^{13}$C-NMR data, HMBC NMR data and NOESY NMR data for arteminolide A, B, C, D, E and F are shown in Tables 6, 7, 8, 9, 10 and 11, respectively(see FIGS. 4, 5 and 6 for $^1$H-NMR, $^{13}$C-NMR and Cosy NMR spectra of arteminolide A, respectively).

TABLE 6

| # | H | C | HMBC | NOESY |
|---|---|---|------|-------|
| 1 | | 134.15 | | |
| 2 | | 194.77 | | |
| 3 | 6.19, brs | 136.25 | 5 | |
| 4 | | 170.08* | | |
| 5 | 3.26 (brd, J=10.3 Hz) | 51.95 | 4, 6 | 7 |

TABLE 6-continued

NMR analysis results for arteminolide A

| # | H | C | HMBC | NOESY |
|---|---|---|------|-------|
| 6 | 4.02 (dd, J=10.7, 9.8 Hz) | 80.13 | | 8 |
| 7 | 2.72 (dd, J=11.3, 10.7 Hz) | 59.40 | 5, 6, 8, 11 | 5 |
| 8 | 4.78 (ddd, J=11.3, 10.7, 2.7 Hz) | 68.14 | | 6 |
| 9 | 2.48 (dd, J=13.2, 10.3 Hz) 2.29 (dd, J=13.2, 2.4 Hz) | 44.55 | | |
| 10 | | 143.65 | | |
| 11 | | 61.31 | | |
| 12 | | 178.41 | | |
| 13 | 2.59 (d, J=11.2 Hz) 1.88 (d, J=11.7 Hz) | 40.33 | 12, 2' | |
| 14 | 2.32, s | 20.28* | 3, 4 | |
| 15 | 2.40, s | 20.51* | 1, 9, 10 | |
| 1' | | 62.91 | | |
| 2' | 5.84, AB | 137.56 | | |
| 3' | 5.84, AB | 136.40 | 11 | |
| 4' | | 57.93 | | |
| 5' | 3.08 (d, J=9.8 Hz) | 66.92 | 11, 1', 2', 3', 6', 7' | 7', 14' |
| 6' | 3.98 (dd, J=9.8, 9.3 Hz) | 79.07 | 1', 8' | |
| 7' | 3.29, m | 43.14 | | 4', 14' |
| 8' | 2.23, m 1.42, m | 23.57 | | |
| 9' | 1.84, m 1.77, m | 34.67 | | |
| 10' | | 72.57 | | |
| 11' | | 140.60 | | |
| 12' | | 170.31 | | |
| 13' | 6.06 (d, J=3.4 Hz) 5.33 (d, J=2.9 Hz) | 118.76 | 7', 12' | |
| 14' | 1.48, s | 17.02 | 11, 3' | 7', 4' |
| 15' | 1.30, s | 29.87 | 1', 9', 10' | |
| 1" | | 171.04 | | |
| 2" | 2.07, m | 43.77 | | |
| 3" | 2.09, m | 25.57 | | |
| 4" | 0.95 (d, J=5.9 Hz) | 22.49* | 2", 3" | |
| 5" | 0.98 (d, T=6.4 Hz) | 22.59* | 2", 3" | |

TABLE 7

NMR analysis results for arteminolide B

| # | H | C | HMBC | NOESY |
|---|---|---|------|-------|
| 1 | | 133.96 | | |
| 2 | | 194.81 | | |
| 3 | 6.19, (dd J=1.5, 1.0 Hz) | 137.64 | 1, 2, 4, 5, 15 | |
| 4 | | 170.06 | | |
| 5 | 3.26 (brd, J=10.3 Hz) | 52.06 | 1, 4, 6 | 7 |
| 6 | 4.03 (dd, J=10.7, 10.3 Hz) | 80.21 | 1 | 8 |
| 7 | 2.70 (dd, J=11.3, 10.7 Hz) | 59.69 | 5, 6, 8, 11, 4' | 5 |
| 8 | 4.77 (ddd, 10.7, 10.7, 2.4 Hz) | 67.31 | | 6 |
| 9 | 2.47 (dd, J=13.2, 10.3 Hz) 2.35 (dd, J=13.7, 2.3 Hz) | 44.69 | | |
| 10 | | 144.12 | | |
| 11 | | 61.34 | | |
| 12 | | 178.46 | | |
| 13 | 2.56 (d, J=11.7 Hz) 1.92, (d, J=11.5 Hz) | 40.16 | 11, 12, 1', 2', 10' | |
| 14 | 2.32, s | 20.42* | | |
| 15 | 2.42, s | 20.63* | 1, 9, 10 | |
| 1' | | 62.91 | | |
| 2' | 5.73 (d, J=5.9 Hz) | 137.64 | 1', 4', 5' | |
| 3' | 5.82, (d, J=5.4 Hz) | 135.93 | 1', 4', 5' | |
| 4' | | 58.11 | | |
| 5' | 3.03 (d, J=10.3 Hz) | 66.93 | 1', 2', 3', 6', 7' | 7', 14' |
| 6' | 3.97 (dd, J=10.3, 9.8 Hz) | 79.10 | 8' | |
| 7' | 3.29, m | 43.15 | | 4', 14' |
| 8' | 2.23, m 1.41, m | 23.67 | | |

TABLE 7-continued

NMR analysis results for arteminolide B

| # | H | C | HMBC | NOESY |
|---|---|---|------|-------|
| 9' | 1.83 (ddd, J=15.1, 8.8, 2.0 Hz) 1.74 (ddd, J=15.1, 10.3, 7.8 Hz) | 34.72 | | |
| 10' | | 72.66 | | |
| 11' | | 140.63 | | |
| 12' | | 170.29* | | |
| 13' | 6.06 (d, J=3.4 Hz) 5.32 (d, J=3.4 Hz) | 118.67 | 7', 11' | |
| 14' | 1.47, s | 17.03 | | 7', 4' |
| 15' | 1.26, s | 29.67 | 1', 9', 10' | |
| 1" | | 164.28 | | |
| 2" | 5.48 (dd, J=1.5, 1.0 Hz) | 115.73 | 4", 5" | |
| 3" | | 158.76 | | |
| 4" | 2.21 (d, J=1.0 Hz) | 20.32 | 2", 3", 5" | |
| 5" | 1.90 (d, J=1.1 Hz) | 27.51 | 2", 3", 4" | |

TABLE 8

NMR analysis results for arteminolide C

| # | H | C | HMBC | NOESY |
|---|---|---|------|-------|
| 1 | | 134.12 | | |
| 2 | | 194.79 | | |
| 3 | 6.19 (dd, J=1.5, 1.0 Hz) | 136.21 | 1, 2, 4, 5 | |
| 4 | | 170.05 | | |
| 5 | 3.29 (brd, J=10.3 Hz) | 51.98 | 4, 6 | 7 |
| 6 | 4.04 (dd, J=10.7, 10.3 Hz) | 80.25 | | 8 |
| 7 | 2.79 (dd, J=10.7, 10.7 Hz) | 59.55 | 6, 8, 11 | 5 |
| 8 | 4.87 (ddd, J=10.7, 10.7, 2.4 Hz) | 67.81 | | 6 |
| 9 | 2.54 (dd, J=12.7, 10.7 Hz) 2.34 (dd, J=13.2, 2.5 Hz) | 44.82 | 1, 8, 10, 15 | |
| 10 | | 143.87 | | |
| 11 | | 61.23 | | |
| 12 | | 178.50 | | |
| 13 | 2.59 (d, J=11.2 Hz) 1.85 (d, J=11.2 Hz) | 40.51 | 12, 1', 2' | |
| 14 | 2.32, s | 20.31* | 3, 4, 5 | |
| 15 | 2.40, s | 20.52* | 1, 9, 10 | |
| 1' | | 63.00 | | |
| 2' | 5.65 (d, J=5.9 Hz) | 137.68 | 1', 3' | |
| 3' | 5.83 (d, J=5.4 Hz) | 136.00 | 1', 2' | |
| 4' | | 58.02 | | |
| 5' | 3.06 (d, J=10.3 Hz) | 66.64 | 1', 2', 3', 6', 7' | 7', 14' |
| 6' | 3.98 (dd, J=9.8, 9.8 Hz) | 79.18 | | |
| 7' | 3.28, m | 43.13 | | 4', 14' |
| 8' | 2.22, m 1.40, m | 23.59 | | |
| 9' | 1.82, m 1.73, m | 34.69 | | |
| 10' | | 72.58 | | |
| 11' | | 140.63 | | |
| 12' | | 170.32* | | |
| 13' | 6.05 (d, J=3.4 Hz) 5.31 (d, J=2.9 Hz) | 118.67 | 7', 12' | |
| 14' | 1.48, s | 17.02 | 11, 3', 4', 5' | 7', 4' |
| 15' | 1.22, s | 29.69 | 1', 9', 10' | |
| 1" | | 165.75 | | |
| 2" | | 127.44 | | |
| 3" | 6.15 (brdq, J=1.5, 7.3 Hz) | 139.99 | 1", 5" | 5" |
| 4" | 2.03 (dq, J=7.3, 1.5 Hz) | 15.99 | 1", 2", 3" | |
| 5" | 1.83 (brq, J=1.5 Hz) | 20.52 | 1", 2", 5" | 3" |

TABLE 9

NMR analysis results for arteminolide D

| # | 1H | 13C | HMBC(H—C, XHz) | NOE |
|---|---|---|---|---|
| 1 | | 134.08 | | |
| 2 | | 194.78 | | |
| 3 | 6.22, (br s) | 136.19 | 1, 2, 4, 5, 14 | 14 |
| 4 | | 170.05 | | |
| 5 | 3.30, (d, J=10.3) | 52.02 | 1, 6, 7 | 7, 9(2.52), 14 |
| 6 | 4.07, (dd, J=10.7, 10.3) | 80.20 | 1 | 8, 14' |
| 7 | 2.80, (dd, J=10.7, 10.7) | 59.74 | 5, 6, 8, 9, 11, 13, 4' | 5, 9(2.52), 13(1.88) |
| 8 | 4.89, (ddd, J=10.7, 10.7, 2.4) | 68.13 | | 6, 9(2.31), 3', 14' |
| 9 | 2.52, (J=dd, 13.2, 10.7) | 44.68 | 1, 7, 8, 10, 15 | 5, 7 |
| | 2.31, (J=dd, 13.2, 2.4) | | 1, 7, 8, 10, 15 | 8 |
| 10 | | 143.91 | | |
| 11 | | 61.31 | | |
| 12 | | 178.44 | | |
| 13 | 2.61, (d, J=11.2) | 40.60 | 12, 1', 2', 4', 10, | 5', 15' |
| | 1.88, (d, J=11.2) | | 11, 12, 1', 2', 4', 5', 6' | 7 |
| 14 | 2.35, s | 20.34 | 2, 3, 4, 5 | 3, 5 |
| 15 | 2.42, s | 20.53 | 1, 2, 9, 10 | |
| 1' | | 63.04 | | |
| 2' | 5.65, (d, J=5.4) | 137.37 | 1', 3', 5' | 3', 6', 9'(1.76), 15' |
| 3' | 5.83, (d, J=5.4) | 136.06 | 1', 2', 5', 14' | 8, 2', 6', 14' |
| 4' | | 58.13 | | |
| 5' | 3.08, (d, J=9.8) | 66.71 | 11, 1', 2', 6', 7' | 13(2.61), 7', 14' |
| 6' | 3.98, (dd, J=9.8, 9.8) | 79.10 | 8' | 2', 3', 8'(1.42), 9'(1.76), 14' |
| 7' | 3.31, m | 43.13 | 12' | 5', 8'(2.23), 13'(5.34) |
| 8' | 2.23, m | 23.60 | | 7', 13'(5.34) |
| | 1.42, m | | | 6', 13'(5.34) |
| 9' | 1.80, m | 34.69 | 1', 7', 10', 15' | |
| | 1.76, m | | | 2', 6', 15' |
| 10' | | 72.59 | | |
| 11' | | 140.60 | | |
| 12' | | 170.28 | | |
| 13' | 6.08, (d, J=3.9) | 118.68 | 7', 11', 12' | 13'(5.34) |
| | 5.34, (d, J=2.9) | | 7', 12' | 7', 8'(2.23, 1.42), 13'(6.08) |
| 14' | 1.51, s | 17.06 | 11, 3', 4', 5' | 6, 8, 3', 5', 6' |
| 15' | 1.22, s | 29.89 | 1', 9', 10' | 13(2.61), 2', 9'(1.76) |
| 1" | | 165.70 | | |
| 2" | | 128.84 | | |
| 3" | 6.76, (dq, J=6.9, 1.2) | 138.27 | 1", 4", 3" | 4" |
| 4" | 1.80, (brd, J=7.3) | 14.50 | 2", 3" | 3" |
| 5" | 1.85, brs | 12.15 | 1", 2", 3" | |

TABLE 10

NMR analysis results for arteminolide E

| # | H | C | HMBC | NOESY |
|---|---|---|---|---|
| 1 | | 134.00 | | |
| 2 | | 194.83 | | |
| 3 | 6.20, br s | 136.22 | 1, 2, 4, 5, 14 | 14 |
| 4 | | 170.88 | | |
| 5 | 3.52 (d, J=10.3 Hz) | 50.46 | 1, 2, 3, 6, 10, 14 | 7, 9, 14 |
| 6 | 3.73 (dd, J=10.3, 9.8 Hz) | 79.26 | 1, 11 | 8, 13 |
| 7 | 2.98 (dd, J=10.3, 10.3 Hz) | 56.37 | 5, 6, 8, 9, 11, 13, 4' | 5, 9, 14' |
| 8 | 5.16 (ddd, 10.3, 10.3, 2.0 Hz) | 65.71 | 7, 9, 10, 11, 1" | 6, 9, 13, 5' |
| 9 | 2.84 (dd, J=13.2, 10.3 Hz) | 44.31 | 1, 7, 8, 10, 15 | 5, 7 |
| | 2.33 (dd, J=13.2, 2.0 Hz) | | 7, 10 | 8 |
| 10 | | 143.98 | | |
| 11 | | 60.12 | | |
| 12 | | 176.40 | | |
| 13 | 2.37 (d, J=11.7 Hz) | 36.15 | 7, 11, 12, 1', 2', 10' | 6, 8 |
| | 1.53 (d, 11.7 Hz) | | 12, 2' | 6, 2', 15' |
| 14 | 2.32, br s | 20.28 | 2, 3, 4, 5 | 3, 5 |
| 15 | 2.42, s | 19.93 | 1, 2, 9, 10 | |
| 1' | | 63.52 | | |
| 2' | 5.80 (d, J=5.7 Hz) | 131.92 | 1', 3', 4', 5', 10' | 13, 3', 6', 9', 15' |
| 3' | 6.37 (d, 5.7 Hz) | 142.45 | 1', 2', 4', 5', 14' | 2', 6', 14' |
| 4' | | 57.26 | | |
| 5' | 2.04 (d, J=9.8 Hz) | 66.26 | 11, 13, 1', 2', 3', 6', | 8, 7', 14' |
| 6' | 4.12 (dd, J=9.8, 9.8 Hz) | 79.23* | 7' | 2', 3', 8', 9', 14' |
| 7' | 2.90, m | 43.08 | 4', 5', 7', 8' | 5', 8' |

TABLE 10-continued

NMR analysis results for arteminolide E

| # | H | C | HMBC | NOESY |
|---|---|---|------|-------|
| 8' | 2.19, m | 23.73 | 5', 6', 8', 11' | 7', 13' |
|  | 1.43, m |  | 6', 9' | 6', 13' |
| 9' | 1.80, m | 34.69 | 7' | 2', 6', 15' |
| 10' |  | 72.50 | 1', 7', 8', 10', 15' |  |
| 11' |  | 141.24 |  |  |
| 12' |  | 169.88 |  |  |
| 13' | 6.05 (d, J=2.9 Hz) | 118.33 |  |  |
|  | 5.32 (d, J=2.9 Hz) |  | 7', 11, 12' | 8' |
| 14' | 1.57, s | 14.74 | 7', 12' | 7, 3', 5', 6' |
| 15' | 1.29, s | 29.73 | 11, 1', 3', 4' | 13, 2', 9' |
| 1" |  | 166.21 | 1', 9', 10' |  |
| 2" |  | 126.88 |  |  |
| 3" | 6.05, m | 142.32 |  | 4", 5" |
| 4" | 1.91 (brd, J=7.8 Hz) | 15.92 | 1", 2", 4", 5" | 3" |
| 5" | 1.92, s | 20.14 | 2", 3' | 5" |
|  |  |  | 1", 2", 3" |  |

TABLE 11

NMR analysis result for arteminolide F

| # | H | C | HMBC | NOESY |
|---|---|---|------|-------|
| 1 |  | 134.17 |  |  |
| 2 |  | 194.77 |  |  |
| 3 | 6.19, br s | 136.16 | 1, 2, 4, 5, 14 | 14 |
| 4 |  | 170.87 |  |  |
| 5 | 3.49 (d, J=9.8 Hz) | 50.31 | 1, 2, 3, 4, 6, 7, 10, 14 | 7, 9, 14 |
| 6 | 3.71 (dd, J=10.3, 9.8 Hz) | 79.17 | 1, 7 | 8, 13 |
| 7 | 2.98 (dd, J=10.3, 10.3 Hz) | 56.65 | 5, 6, 8, 9, 13 | 5, 9, 14' |
| 8 | 5.02 (ddd, J=10.3, 10.3, 2.0 Hz) | 65.10 | 7, 10, 11, 1" | 6, 9, 13, 5' |
| 9 | 2.77 (dd, J=13.2, 10.3 Hz) | 43.79 | 1, 7, 8, 10, 15 | 5, 7 |
|  | 2.32 (dd, J=13.2, 2.0 Hz) |  | 1, 7, 8, 10, 15 | 6, 8 |
| 10 |  | 143.56 |  |  |
| 11 |  | 60.02 |  |  |
| 12 |  | 176.24 |  |  |
| 13 | 2.34 (d, J=12.0 Hz) | 36.53 | 7, 11, 12, 1' | 6, 8 |
|  | 1.56 (d, J=12.0 Hz) |  | 12, 2', 10 | 6, 2', 15' |
| 14 | 2.31, br s | 20.28 | 2, 3, 4, 5 | 3, 5 |
| 15 | 2.42, s | 20.00 | 1, 2, 9, 10 |  |
| 1' |  | 63.20 |  |  |
| 2' | 5.80 (d, J=5.7 Hz) | 131.77 | 1', 3', 4', 5' | 13, 3', 9', 15' |
| 3' | 6.40 (d, J=5.7 Hz) | 142.88 | 1', 2', 4', 5', 14' | 2', 14' |
| 4' |  | 57.30 |  |  |
| 5' | 1.98 (d, J=9.8 Hz) | 66.34 | 11, 13, 1', 2', 3', 6', 7' | 8, 7', 14' |
| 6' | 4.18 (dd, J=9.8, 9.8 Hz) | 79.53 | 7', 8' | 8', 9', 14' |
| 7' | 3.06, m | 43.28 | 6', 8', 11' | 5', 8', 13' |
| 8' | 2.19, m | 23.70 | 6', 7', 9', 10' | 7', 13' |
|  | 1.46, m |  | 7' | 6', 13' |
| 9' | 1.83, m | 34.85 | 1', 7', 8', 10', 15' | 2', 6', 15' |
| 10' |  | 72.56 |  |  |
| 11' |  | 140.86 |  |  |
| 12' |  | 170.29 |  |  |
| 13' | 6.11 (d, J=3.4 Hz) | 119.34 | 7', 11', 12' |  |
|  | 5.38 (d, J=3.4 Hz) |  | 11', 12' | 7', 8' |
| 14' | 1.56, s | 14.56 | 11, 3', 4', 5' | 7, 3', 5', 6' |
| 15' | 1.29, s | 29.80 | 1', 9', 10' | 9, 13, 2' |
| 1" |  | 172.17 |  |  |
| 2" | 2.21, m | 43.46 | 1", 3", 4", 5" | 4", 5" |
|  | 2.04, m |  |  |  |
| 3" | 2.04, m | 25.82 | 4", 5", |  |
| 4" | 0.96 (d, J=6.4 Hz) | 22.30a | 2", 3", 5" | 2" |
| 5" | 0.93 (d, J=6.8 Hz) | 22.16a | 2", 3", 4" | 2" |

EXAMPLE 3

Assay for Farnesyl-protein Transferase Inhibiting Activity of Arteminolide Compounds Farnesyl-protein transferase activity was determined in accordance with the scintillation proximity assay method of Blown et al. described in *Cell*, 62, 1(1990) by using $^3$H-farnesyl pyrophosphate(FPP) as a substrate.

First, a cerebrum obtained from white rat(male Spraguo Dowley 100–150 g) was washed with physiological saline solution and homogenized. The homogenized solution was centrifuged and partially purified by using Q sepharose fast flow column to obtain farnesyl protein transferase(FPTase).

10 μl of a sample, 40 μl of FPTase obtained above, 10 μl of an assay buffer(50 mM Tris-HCl, pH 7.5, 25 mM $MgCl_2$, 2 mM KCl, 5 mM DTT, 5 mM $Na_2HPO_4$, 0.01% Triton X-100), 20 μl of diluted $^3$H-FPP and 20 μl of biotin-lamin B peptide were mixed together and the resulting mixture was reacted at room temperature for 30 minutes. 150 μl of SPA bead/stop reagent solution was added to the mixture and the enzymatic activity was determined by examining the extent of biotin lamin B peptide farneslyation, expressed by a unit of count per minute(CPM), with a liquid scintillation counter.

The FPTase inhibiting activity was then calculated in accordance with the following equation:

$$\text{Degree of Inhibition}(\%) = 100 \times \left[ 1 - \frac{CPM(\text{sample}) - CPM(\text{blank})}{CPM(\text{control}) - CPM(\text{blank})} \right]$$

wherein the blank had the same composition as the sample except that the enzyme and arteminolide compound were not used, and the control had the same composition as the sample except that the arteminolide compound was not present.

The $IC_{50}$ values of arteminolide compounds calculated from the degree of inhibiting are shown in Table 12.

TABLE 12

$IC_{50}$ values of Arteminolide Compounds for FPTase Inhibition

| Compound | $IC_{50}(\mu M)$ |
|---|---|
| A | 0.38 |
| B | 0.40 |
| C | 0.74 |
| D | 0.63 |
| E | 150 |
| F | 160 |

EXAMPLE 4

Assay for Angiogenesis Suppressing Activity of Arteminolide Compounds

Angiogenesis was determined in accordance with the chorioallantoic membrane(CAM) assay method of Kusaka et al. described in *Biochem. Biophy. Res. Comm.*, 174, 1070(1991) by using a fertilized chicken egg.

1) day 1(0 day-embryo)

A fertilized chicken egg(Pulmuwon co., Korea) was incubated at 37°–38° C. and a humidity of more than 90%. Here, 0 day-embryo means that the fertilized egg had been storaged at 18° C. for no more than 3–4 days since laying.

2) day 3(2 day-embryo)

The pointed end of the fertilized egg was scratched with a knife, laid horizontally, the scratched site was punctured with a 5 ml syringe and 2 ml of albumin was extracted from the fertilized egg. The puncture hole was then sealed with a glass-tape. The fertilized egg, laid such that the sealed hole is located at the bottom, was incubated under the same condition described above.

3) day 4(3 day-embryo)

The other end of the fertilized egg where the air sac is located, i.e., the end opposite to the hole site was opened, a window having a diameter of 2–3 cm was installed therein, the window was sealed with a glass-tape, and the incubation was resumed.

4) day 5(4.5 day-embryo)

At this time, a chorioalletoic membrane(CAM) of 2–5 mm diameter develop. A arteminolide sample was dissolved in distilled water or ethanol, 10 μl of the sample solution was dropped on quartered Thermanox coverslip(Nunc, Co.,) and dried in a clean bench. The sealing glass-tape was removed, the treated Thermanox coverslip obtained above was laid on the CAM and then sealed with a glass-tape. All tools used in the above procedure were pre-sterilized with 70% ethanol.

5) day 7(6.5 day-embryo)

The sealing glass-tape was removed. 1 ml of Intralipose (fat emulsion, Green Cross co., Korea) was taken with syringe, removed an air bobble therefrom and injected into an area below the CAM.

Angiogenesis suppressing activity was then calculated in accordance with the following equation:

$$\text{Degree of suppression}(\%) = 100 \times \frac{\text{number of eggs showing angiogenesis suppression at } CAM}{\text{number of eggs tested}}$$

The $IC_{50}$ values of arteminolide compounds calculated from the degree of suppressing are shown in Table 13.

TABLE 13

$IC_{50}$ values of Arteminolide Compounds for Angiogenesis Suppression

| Compound | $IC_{50}(\mu M)$ |
|---|---|
| A | 5.4 |
| B | 5.2 |
| C | 0.5 |
| D | 6.2 |
| E | 20 |
| F | 24 |

While the invention has been described with respect to the above specific embodiments, it should be recognized that various modifications and changes may be made and also fall within the scope of the invention as defined by the claims that follow.

What is claimed is:

1. A substantially pure arteminolide compound of formula (I) or (II):

wherein R¹ is and R² is

2. A process for the preparation of the arteminolide compound of claim 1, comprising the steps of:

(a) disrupting *Artemisia sylvatica* MAXIMOWICZ and extracting it with an organic solvent to obtain an extract;

(b) subjecting the extract to silica gel chromatography to obtain a fraction containing a mixture of arteminolide compounds; and

(c) subjecting the mixture to high performance liquid chromatography to obtain the arteminolide compound in a pure form.

3. A pharmaceutical composition, comprising therapeutically effective amount of a substantially pure arteminolide compound of formula (I) or (II):

wherein R¹ is and R² is a pharmaceutically acceptable carrier.

* * * * *